US012720664B2

(12) United States Patent
Wandke et al.

(10) Patent No.: US 12,720,664 B2
(45) Date of Patent: Aug. 25, 2026

(54) ELECTRODE ASSEMBLY FOR A PLASMA DISCHARGE

(71) Applicant: CINOGY GMBH, Duderstadt (DE)

(72) Inventors: Dirk Wandke, Heilbad Heiligenstadt (DE); Ronny Lettke, Duderstadt (DE)

(73) Assignee: CINOGY GMBH, Duderstadt (DE)

(*) Notice: Subject to any disclaimer, the term of this patent is extended or adjusted under 35 U.S.C. 154(b) by 0 days.

(21) Appl. No.: 18/692,004

(22) PCT Filed: Sep. 21, 2022

(86) PCT No.: PCT/EP2022/076177
§ 371 (c)(1),
(2) Date: Mar. 14, 2024

(87) PCT Pub. No.: WO2023/046726
PCT Pub. Date: Mar. 30, 2023

(65) Prior Publication Data

US 2025/0133645 A1 Apr. 24, 2025

(30) Foreign Application Priority Data

Sep. 21, 2021 (DE) ..................... 10 2021 124 377.7

(51) Int. Cl.
*H05H 1/24* (2006.01)
*A61N 1/44* (2006.01)

(52) U.S. Cl.
CPC ............. *H05H 1/2418* (2021.05); *A61N 1/44* (2013.01); *H05H 2245/34* (2021.05)

(58) Field of Classification Search
None
See application file for complete search history.

(56) References Cited

U.S. PATENT DOCUMENTS 9,287,762 B2 * 3/2016 Kamata ................ H05H 1/2406
9,691,873 B2 * 6/2017 Rogers .................... H10D 48/30
11,582,856 B2 * 2/2023 Polak ......................... A61L 2/14
2006/0042545 A1 * 3/2006 Shibata ............. H01J 37/32009 118/722
2011/0287193 A1 * 11/2011 Creyghton ........... H05H 1/2439 118/723 R (Continued)

FOREIGN PATENT DOCUMENTS

CN 107124810 A 9/2017
DE 103 24 926 B3 2/2005

(Continued)

*Primary Examiner* — Srinivas Sathiraju
(74) *Attorney, Agent, or Firm* — WCF IP

(57) ABSTRACT

An electrode arrangement for forming a dielectric barrier discharge between at least one electrode and a surface to be treated of an electrically conductive body, said surface acting as a ground electrode, with a dielectric that completely covers the electrode to the surface to be treated, said dielectric forming a contact side for the surface to be treated, and with a control device that comprises a high-voltage stage for supplying the electrode with an alternating high voltage required for generating the plasma, said control device emitting the alternating high voltage to the electrode in the form of individual pulse signals, characterized in that the control device is configured to generate two successive opposite-pole pulse signals.

7 Claims, 4 Drawing Sheets

(56) References Cited

U.S. PATENT DOCUMENTS

Figure 1:
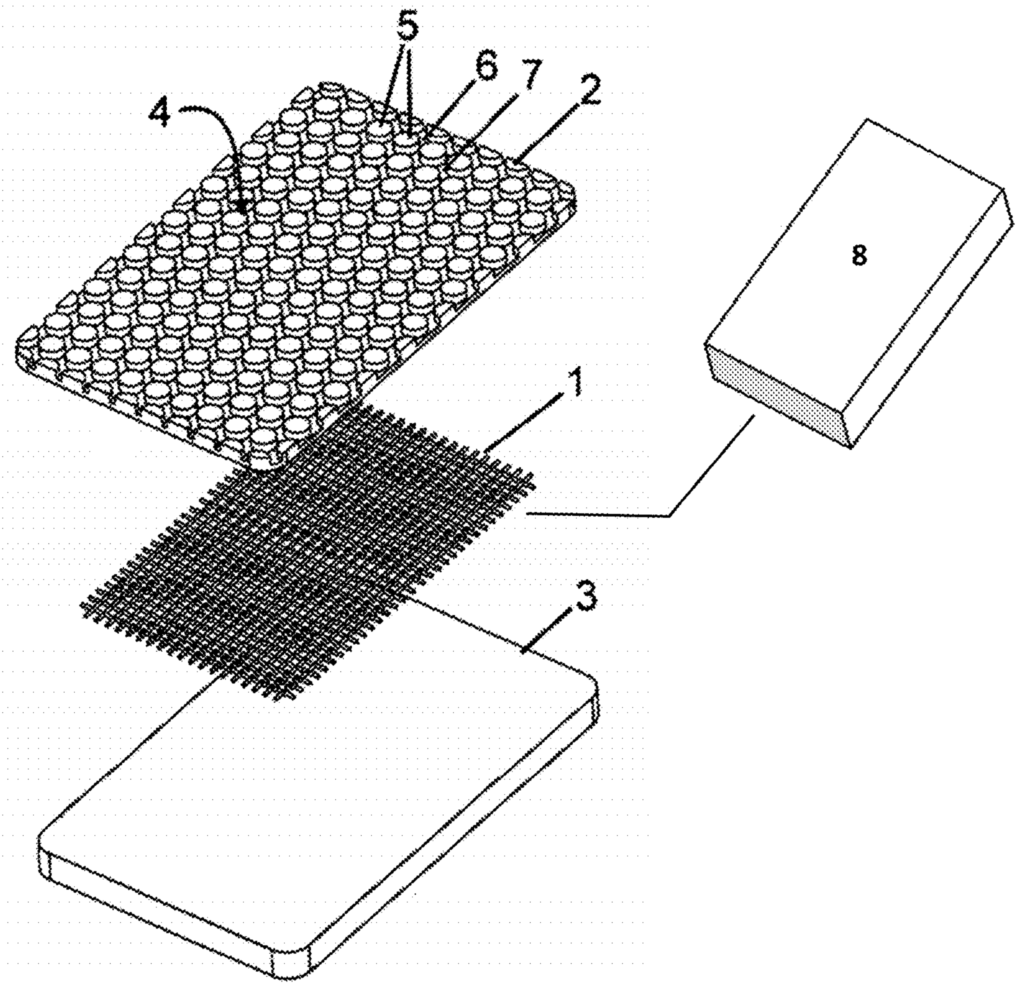

2012/0259270 A1* 10/2012 Wandke .................. A61N 1/40 604/23
2016/0020704 A1* 1/2016 Fujita .................. H02M 7/537 363/37
2016/0081175 A1* 3/2016 Kamata .................. H02M 7/539 315/111.21
2016/0236002 A1* 8/2016 Dirk .................. A61N 1/44
2016/0242269 A1* 8/2016 Dirk .................. H05H 1/2406
2017/0354453 A1* 12/2017 Krasik .................. A61B 1/018
2018/0221517 A1* 8/2018 Trutwig .................. A61L 2/02
2018/0295708 A1* 10/2018 Trutwig .................. A61L 2/14
2019/0157044 A1* 5/2019 Ziemba .................. H03K 3/021
2019/0223280 A1* 7/2019 Wandke .................. A61N 1/44
2020/0029414 A1* 1/2020 Trutwig .................. A61B 18/042
2020/0038530 A1* 2/2020 Yildirim .................. A61L 2/14
2020/0170098 A1* 5/2020 Wandke .................. H05H 1/2406
2020/0187341 A1* 6/2020 Wandke .................. A61L 2/14
2020/0221564 A1* 7/2020 Wandke .................. A61L 2/26
2021/0022234 A1* 1/2021 Polak .................. A61L 2/14
2021/0249227 A1* 8/2021 Bowman .................. H02M 3/33592
2021/0338304 A1* 11/2021 Krasik .................. A61B 1/018
2022/0172929 A1* 6/2022 Wandke .................. H05H 1/2406
2022/0304132 A1* 9/2022 Wandke .................. H05H 1/2406
2023/0165624 A1* 6/2023 Polak .................. A61N 1/44 604/23
2024/0374765 A1* 11/2024 Damm .................. A61L 2/08
2025/0133645 A1* 4/2025 Wandke .................. H05H 1/2418

FOREIGN PATENT DOCUMENTS

DE 10 2006 011 312 A1 10/2007
DE 10 2012 025 082 B3 1/2014
DE 10 2016 118 569 A1 4/2018
KR 2014 0099 726 A 8/2014
WO 2004/105810 A1 12/2004
WO WO-2004107394 A2 * 12/2004 .................. H10P 50/242
WO WO-2012097904 A2 * 7/2012 .................. H05H 1/2406
WO 2019/121968 A1 6/2019

* cited by examiner

ELECTRODE ASSEMBLY FOR A PLASMA DISCHARGE

The invention relates to an electrode arrangement for forming a dielectric barrier discharge between at least one electrode and a surface to be treated of an electrically conductive body, said surface acting as a ground electrode, with a dielectric that completely covers the electrode to the surface to be treated, said dielectric forming a contact side for the surface to be treated, and with a control device for supplying the electrode with an alternating high voltage that emits said alternating high voltage to the electrode in the form of individual pulse signals.

Such a two-dimensional electrode arrangement is known, for example, from DE 103 24 926 B3, which is configured to treat a biological material containing living cells by generating a plasma discharge under atmospheric pressure. With the aid of an alternating high voltage generator, an alternating high voltage is applied to the electrode, so that a dielectric barrier discharge occurs under atmospheric pressure, starting from the electrode and continuing towards the surface of the electrically conductive body to be treated, said surface acting as a ground electrode. In particular, the dielectric is a solid dielectric arranged without any clearance in front of the electrode.

Such an electrode arrangement can be applied with the contact side of the dielectric to the surface to be treated, wherein the surface to be treated can, in particular, be the skin of a human or animal body. The plasma discharge leads to a disinfection of the skin and improves the skin's capacity to absorb conditioning agents applied to the surface to be treated.

EP 3 448 130 A1 also discloses such an electrode arrangement in accordance with the preamble for forming a dielectric barrier plasma discharge. In this case, it is provided for that the electrodes embedded in the dielectric are composed of at least two partial electrodes insulated from each other by the dielectric, wherein neighbouring partial electrodes are supplied by the control device, which in particular contains the alternating high voltage generators, with partial alternating high voltages, which are opposite in terms of waveform and voltage level, and which compensate each other. This means that even comparatively large areas can be treated efficiently and as evenly as possible with plasma at a comparatively low energy input by applying a flexible electrode arrangement in particular. The alternating high voltages preferably oscillate around the ground potential, wherein the compensating partial alternating high voltages of the individual partial electrodes largely create an ideally homogeneous electric field.

When using the skin as a ground electrode in relation to the alternating high voltage potential, if, for example, the distance between the electrode and the skin is too great or the electrode arrangement is energised even though it is not in contact with the skin, the HV potential may not flow off properly and reliably and may be further increased by subsequent voltage pulses of the same polarity. The averaged potential on the electrode shifts further and further towards the polarity of the original triggering pulse, which causes static charging. The ultimate result of this is that the high voltage generator can be affected due to the static charging, meaning that not inconsiderable efforts have to be taken to secure these devices.

DE 10 2016 011 312 A1 discloses a device for treating plasma under atmospheric pressure. Here too, an electrode is shielded from a dielectric in the familiar manner and the electrode is subjected to an alternating high voltage. In this case, the counter electrode is to be abandoned and the gas surrounding the electrode arrangement used instead as a type of counter electrode.

The task of the present invention is therefore to present an improved electrode arrangement with which the issue of static charging known from the prior art can be reduced or possibly entirely eliminated.

According to the invention, the task is solved with the electrode arrangement in accordance with claim 1. Advantageous embodiments of the invention are to be found in the corresponding sub-claims.

According to claim 1, an electrode arrangement in line with the preamble is used to form a dielectric barrier plasma discharge between at least one electrode and a surface to be treated of an electrically conductive body, said surface acting as a ground electrode, the electrode arrangement comprising a dielectric which completely covers the electrode to the surface to be treated and which forms a contact side for the surface to be treated. Furthermore, the electrode arrangement has a control device that is configured to supply or apply an alternating high voltage to the at least one electrode. By applying an alternating high voltage to the electrode embedded in the dielectric and due to the interaction with the electrically conductive body acting as a ground electrode a dielectric barrier plasma discharge is created. The alternating high voltage is generated in the form of individual pulse signals and emitted to the electrode. In addition, the alternating high voltage can be generated in the form of pulse signals with a defined polarity and pulse intervals and emitted to the electrode.

In this case, the control device of the electrode arrangement includes at least one high-voltage stage (alternating high voltage generator), which is designed to generate the alternating high voltage, and a control unit in order to be able to adjust properties of the alternating high voltage and control the high-voltage stage accordingly.

According to the invention, it is now provided that the control device is configured to generate two successive opposite-pole pulse signals in the form of damped oscillations in such a way that the initial half-wave of the first pulse signal has the opposite polarity to the initial half-wave of the subsequent second pulse signal.

In particular, it is therefore provided that the control device emits the alternating high voltage to the electrode in the form of individual pulse signals in such a way that, in the event of a plurality of pulse signals, at least two successive pulse signals are of opposite polarity. In particular, it is provided that the pulse signals with different polarity add up to zero (within tolerances), so that static charging is avoided or reduced as a result.

It is therefore proposed to supply the electrode of the electrode arrangement with an alternating high voltage by means of the control device in such a way that at least two successive pulse signals are of opposite polarity, i.e. are alternating with regard to the waveform and/or voltage level. The two opposite-pole pulse signals should be symmetrically identical. It is intended that the initial half-wave of the first pulse signal is of opposite polarity or opposite to the initial half-wave of the subsequent second pulse signal.

The control device therefore emits the alternating high voltage to the electrode in the form of individual pulse signals in such a way that a second number of second pulse signals follows a first number of first pulse signals, the second pulse signals being of opposite polarity to the first pulse signals. The control device can be configured in such a way that this process is repeated so that the second pulse signals are followed by the first pulse signals again and a new cycle begins. The first number of the first pulse signals can be identical to the second number of the second pulse signals. The number of pulse signals is greater than or equal to 1. If the number of pulse signals is 1, two successive pulse signals are always of opposite polarity. Otherwise, two successive groups, each with a plurality of pulse signals, are of opposite polarity. In this case, the first pulse signals have a first defined polarity, while the second pulse signals have a defined second polarity. In all cases, the signals of various polarity should add up to zero, so that static charging is ultimately avoided or reduced.

In this context, opposite polarity means in particular that the sum DC voltage potential resulting from the first pulse signal is of opposite polarity to the resulting sum DC voltage potential of a subsequent second pulse signal of opposite polarity. According to this, the polarity is inverted between the two successive opposite-pole pulse signals.

The pulse signals in this case have a defined polarity, wherein, due to the generation of opposite-pole pulse signals that have a second polarity inverted to a first polarity, the signals of different polarity add up to zero.

These opposite-pole or alternating pulse signals render it possible to prevent static charging of the electrode arrangement, as successive opposite-pole pulse signals compensate preceding static charging. In the case of pulse signals in the form of damped oscillations in particular, the DC voltage potential is shifted due to the direction or polarity of the initial oscillation. This built-up DC voltage potential can then be compensated accordingly by way of a subsequent opposite-pole pulse signal so that static charging is prevented over time by pulse signals that are generated one after the other and compensate each other.

In contrast to operation with two neighbouring partial electrodes, which are supplied almost simultaneously with two opposite, compensating partial alternating high voltages, the supply of the electrodes with the alternating high voltage in the present invention occurs with only one electrode, so that the individual pulse signals are emitted to the electrode one after the after. Here, the pulse signals are preferably generated by the same alternating high voltage generator of the control device, wherein two consecutive pulse signals have opposite polarity due to alternating activation. This makes it possible to realise an electrode arrangement in single-phase operation in which only one electrode and an alternating high voltage generator for supplying the electrode with an alternating high voltage are provided without the risk of static charging. The components contained within the alternating high voltage generator have tolerances for generating the alternating high voltage. However, since the alternating pulse signals are generated by the same signal-determining components of the alternating high voltage generator, complete compensation of the voltage pulses whilst avoiding static charging can be achieved, since the alternating pulse signals contain the deviation caused by the inherent tolerance of the components in opposite polarity, so that any charges are cancelled out.

It is therefore especially advantageous if the control device is designed to generate the consecutive alternating voltage pulses using the same alternating high voltage generator with the same components.

In the case of a pulse train with damped oscillation, the initial half-wave often has the highest amplitude so that the polarity of this pulse signal is determined by the polarity of the initial half-wave.

The pulse signals can oscillate about a neutral line or zero line such that, starting from this neutral line, a positive half-wave is followed by a negative half-wave, which can then be followed by another positive half-wave, for example. The respective half-waves of the consecutive pulse signals are opposite and thus lead to two consecutive opposite-pole pulse signals.

According to an embodiment, it is provided that the control device emits the pulse signals to the electrode in such a way that a number of pulse signals with a first polarity are emitted one after the other and then the same number of pulse signals with a second polarity opposite to the first are emitted one after the other.

According to an embodiment, it is provided that the number of the pulse signals with the same polarity is smaller than or equal to ten.

This means that a series of pulse signals with a first polarity are emitted to the electrode one after the other, the pulse signals with a second polarity opposite to the first polarity being generated following said series of pulse signals and emitted to the electrode. In accordance with this, n pulse signals with a first polarity are generated and emitted to the electrode, and n pulse signals with an opposite-pole second polarity are generated and emitted to the electrode.

According to an embodiment, it is provided that the ratio of pulse duration of a single pulse signal to the pulse distance of two pulse signals is greater than 1:10, preferably greater than 1:20. Accordingly, the pulse duration is significantly smaller than the pulse distance between two pulse signals. Here, the duty cycle as a ratio of pulse duration to period duration is less than 10%, preferably less than 5%.

According to an embodiment, it is provided that the control device comprises an inverter circuit connected to the high-voltage stage, said circuit being configured to control the high-voltage stage successively in opposite polarity with an electrical voltage to generate two successive opposite-pole pulse signals. Due to the inverter circuit, the high-voltage stage is controlled successively with an inverted polarity so that, following a pulse signal of a certain polarity, a subsequent inverted pulse signal can be generated by the high-voltage stage.

According to an embodiment, it is provided that the control unit emits the alternating high voltage to the electrode in such a way that the electrical power is less than 10 W, preferably less than 5 W; that the voltage pulses are bipolar and/or that the electrical alternating voltage lies between ±1 kV and ±100 kV, preferably between ±2 kV and ±25 kV. The alternating electrical frequency of the damped oscillation preferably lies between 100 Hz and 100 MHz, especially preferably between 1 kHz and 100 MHZ, especially preferably between 10 KHz and 100 MHZ. The frequency of repetition of the pulse signals (formed by the damped oscillation sections) lies between 100 Hz and 10 kHz, preferably between 250 Hz and 1 KHz.

Figure 2:
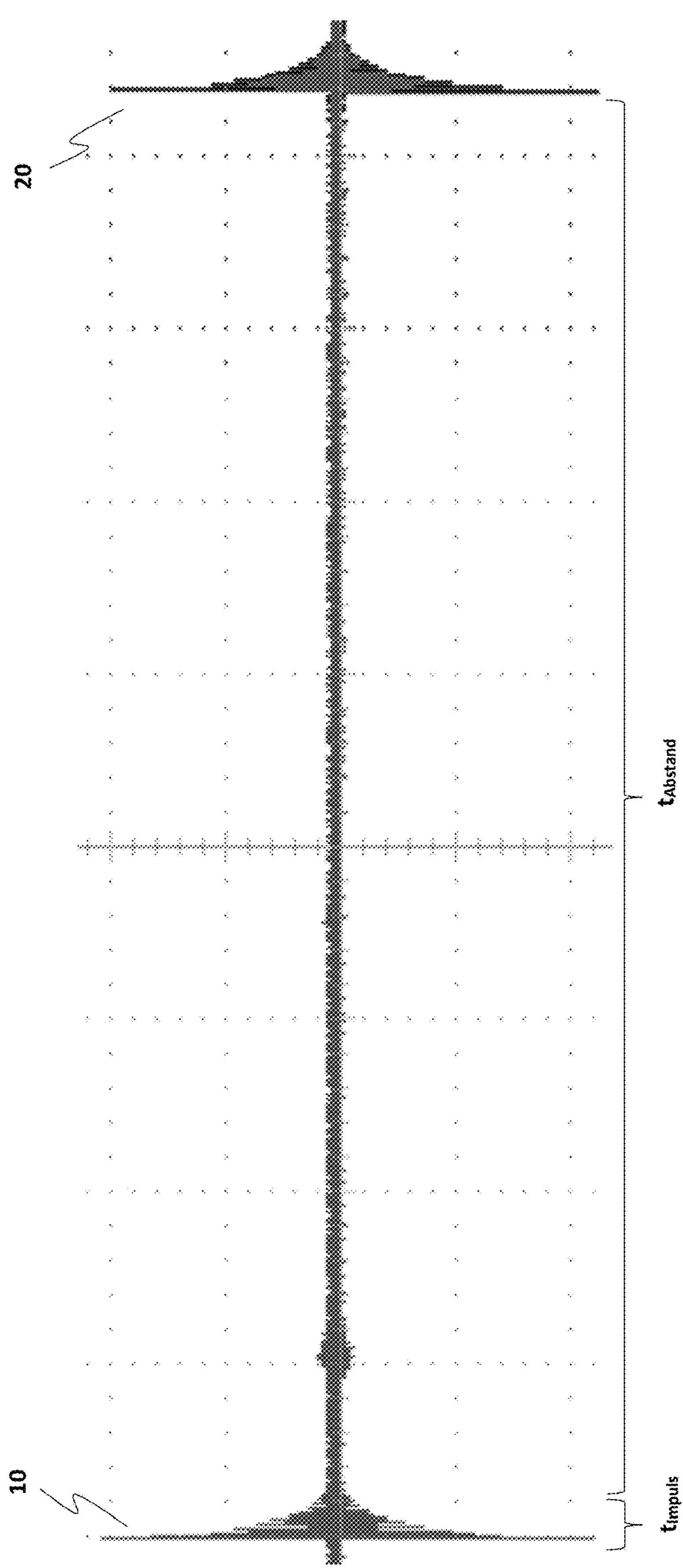
Figure 3A:
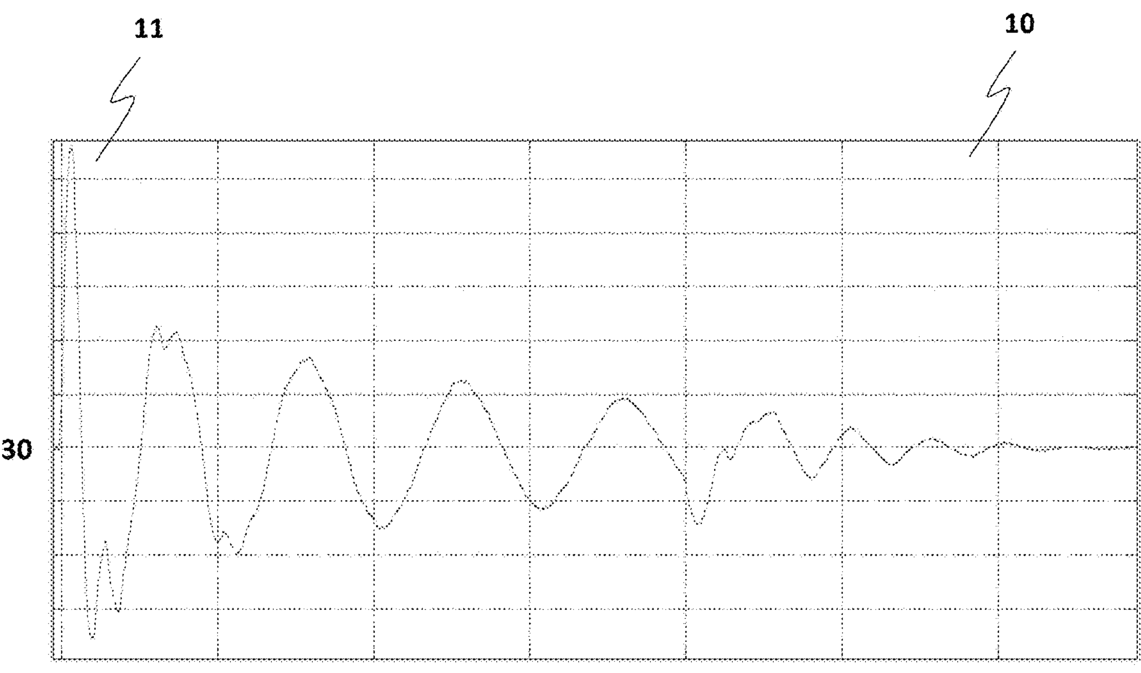
Figure 3B:
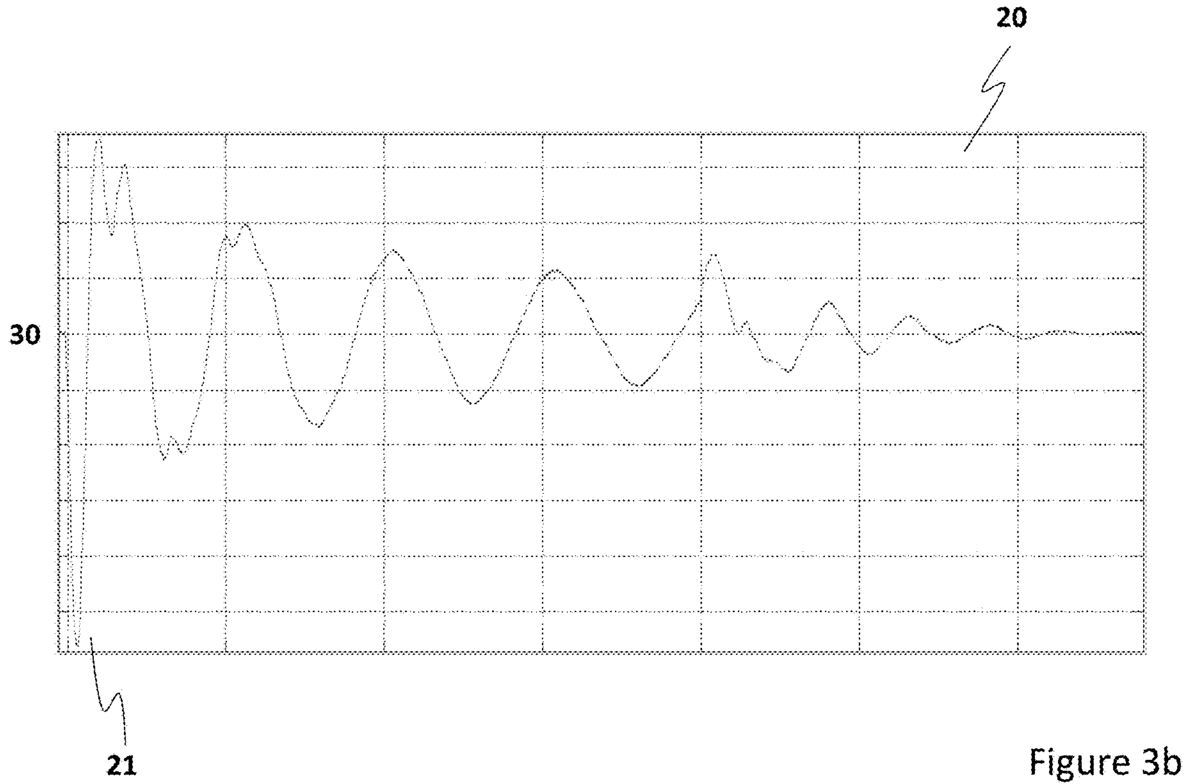
Figure 4:
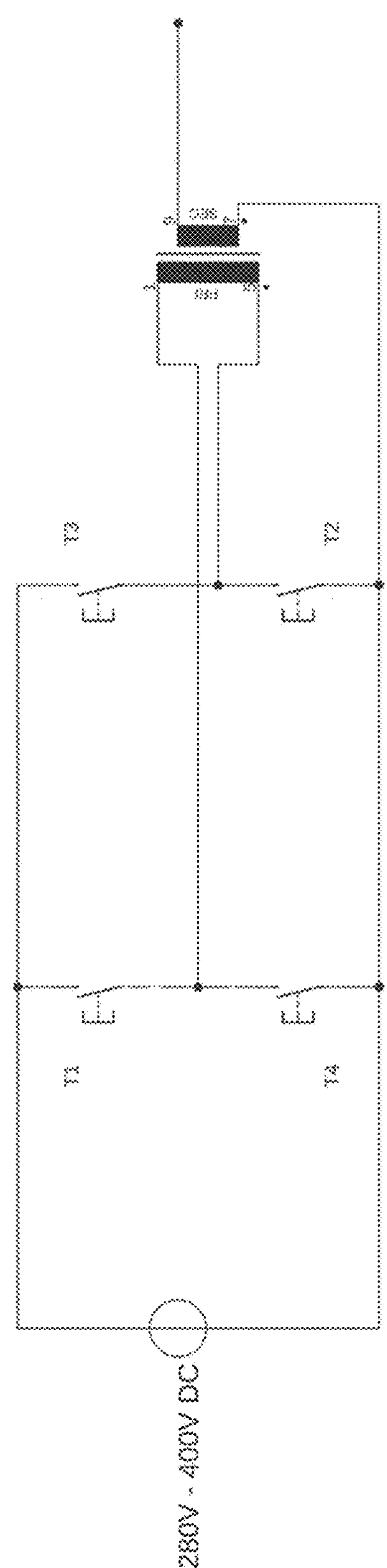

The invention is explained in more detail by means of the attached figures. They show:

FIG. 1 an exploded view of a schematic representation of an electrode arrangement according to the preamble;

FIG. 2 oscillogram of two pulse trains with damped oscillation;

FIG. 3*a*, 3*b* depiction of two opposite-pole pulse signals;

FIG. 4 depiction of an embodiment for an inverter circuit.

In a highly simplified schematic representation, FIG. 1 shows the basic elements of an electrode arrangement according to the preamble with an electrode 1, which can be designed as a flat, flexible electrode grid made of metal in the initial state. Of course, other forms of electrode and other materials are also conceivable. The electrode is arranged between a front layer 2 made of dielectric material and a back layer 3 made of a dielectric material. In the initial state, the two dielectric layers 2, 3 are designed to be planar and flat and protrude over the electrode 1 on all four side edges, such that the electrode 1 is embedded on all sides in the dielectric formed by the two layers 2, 3. To this end, the layers 2, 3 are connected to each other, preferably across their surfaces. Said connection may be achieved, for example, by gluing or welding. Of course, it is also conceivable that the electrode 1 is embedded between the layers 2, 3, the layers 2, 3 being designed integrally as a single body. The electrode 1 embedded in the dielectric can be brought into contact with a connector (not depicted) protruding from the dielectric.

The front layer 2 of the dielectric is equipped with a structured surface 4 on the side facing away from the electrode 1. In the embodiment example shown, the structured surface is formed by protruding nubs, which are at a distance 6 from each other, so that the structured surface 4 comprises numerous connected airflow areas 7 in which air can flow when the electrode arrangement rests with the nubs 5 of its front layers 2 on a surface to be processed, for example the skin of a living being. Alternatively, it is also conceivable that grid walls are provided as a structured surface 4, said walls possibly not permitting any exchange of air.

The electrode arrangement shown in the figure also comprises a control device 8 that is electrically connected to the electrode 1 via an electrical line. The control device 8 has a high-voltage stage (alternating high-voltage generator), not depicted, which can be connected, for example, to an inverter circuit (FIG. 4). The alternating high voltage generator can be used to generate an alternating high voltage, which is then emitted to electrode 1. If the electrode arrangement rests with the structured surface 4 on the electrically conductive body acting as a ground electrode, the dielectric-barrier current flow leads to a plasma discharge of the desired type.

To now prevent static charging, which under certain circumstances may affect the alternating high voltage generator of the control device 8, the electrode 1 is supplied on an alternating basis with opposite, compensating alternating high voltages in the form of pulse signals by controlling the high-voltage stage with an alternating polarity by means of the inverter circuit.

FIG. 2 depicts an oscillogram of two pulse signals 10, 20, wherein the first pulse signal 10 is followed, after an interval (pulse distance), by the generation of a second pulse signal 20, which is emitted to the electrode. It should be noted that the two pulse signals 10, 20 are pulse trains with damped oscillation, where the amplitudes become smaller within the respective pulse signal.

The pulse duration $t_{Impuls}$ of a respective pulse signal is significantly smaller than the interval or pulse distance $t_{Abstand}$ between the two pulse signals 10, 20. The duty cycle, i.e. the ratio between pulse duration and period duration, is preferably below 5%. This duty cycle has delivered good results, whereby it is presumed that the complete recombination of ions formed by the plasma does not yet end at this period duration.

Two pulse signals 10, 20 of opposite polarity are depicted in FIGS. 3*a* and 3*b*. FIG. 3*a* depicts a first pulse signal 10, while FIG. 3*b* shows a subsequent second pulse signal 20. The pulse signals 10, 20 oscillate about a neutral line 30, the pulse peaks swinging in both the positive range and the negative range.

The first pulse signal in FIG. 3*a* begins with an initial half-wave 11 that has a positive charge sign. The half-wave subsequently oscillates about the neutral line 30, wherein the amplitudes weaken as the half-wave progresses. FIG. 3*b* depicts an opposite-pole pulse signal 20, which is opposite, symmetrically identical and of opposite polarity. The initial half-wave 21 of the second pulse signal 20 has a negative charge sign and is otherwise completely symmetrically identical to the initial half-wave 11 of the first pulse signal 10.

Static charging is thus eliminated by the successive, opposite and opposite-pole pulse signals 10, 20, as the pulse signals add up to zero or essentially zero.

Both pulse signals 10, 20 are generated by the same control device with the same alternating high voltage generator so that tolerances during the generation of the alternating high voltages are reflected in both the first pulse signal 10 and the second pulse signal 20. By reversing the charge sign in the two opposite-pole pulse signals 10, 20 using the same alternating high-voltage source, the tolerance-related characteristic properties of the pulse signals are present in both and therefore cancel each other out.

FIG. 4 depicts an inverter circuit of the control device for generating opposite-pole high-voltage pulses. If the switches T1 and T2 are closed and the switches T3 and T4 are open, a positive voltage is applied to the high-voltage transformer from terminal 1 to 5 and from terminal 9 to 7. This enables a first pulse signal to be generated.

Conversely, if the switches T1 and T2 are open and the switches T3 and T4 are closed, a negative voltage is applied to the high-voltage transformer from terminal 1 to 5 and from terminal 9 to 7. Consequently, a second pulse signal opposite to the first pulse signal is generated.

Accordingly, the switches T1 to T4 are controlled by the control device in such a way that the desired resulting pulse signals are formed by the high-voltage transformer.

REFERENCE LIST

1 electrode
2,3 dielectric
4 structured surface
5 nubs
6 distance between the nubs
7 airflow areas
8 control device
10 first pulse signal
11 initial half-wave of the first pulse signal
20 second pulse signal
21 initial half-wave of the second pulse signal
30 neutral line
$t_{Impuls}$ pulse duration
$t_{Abstand}$ pulse distance

The invention claimed is:

1. An electrode arrangement for forming a dielectric barrier discharge between at least one electrode and a surface to be treated of an electrically conductive body, said surface acting as a ground electrode, comprising:

a dielectric that completely covers the at least one electrode to the surface to be treated, wherein said dielectric forms a contact side for the surface to be treated; and a control device that comprises a high-voltage stage for supplying the at least one electrode with an alternating high voltage required for generating a plasma, wherein the control device emits the alternating high voltage to the at least one electrode in individual pulse signals, wherein the control device is configured to generate two successive opposite-pole pulse signals in damped oscillations such that an initial half-wave of a first pulse signal has an opposite polarity to an initial half-wave of a subsequent second pulse signal, and feed the opposite-pole pulse signals successively to the same at least one electrode, and wherein a ratio of pulse duration of a single pulse signal to a pulse distance of two pulse signals is greater than 1:10.

2. The electrode arrangement according to claim 1, wherein the control device emits the alternating high voltage to the at least one electrode in the individual pulse signals such that, in an event of a plurality of pulse signals, at least two successive pulse signals are of opposite polarity.

3. The electrode arrangement according to claim 1 wherein the control device emits the individual pulse signals to the at least one electrode such that a number of pulse signals with a first polarity are emitted one after the other and then a same number of pulse signals with a second polarity opposite to the first polarity are emitted one after the other.

4. The electrode arrangement according to claim 1 wherein the control device generates two successive opposite-pole pulse signals with a common high-voltage stage.

5. The electrode arrangement according to claim 1 wherein the control device comprises an inverter circuit connected to the high-voltage stage, said inverter circuit being configured to control the high-voltage stage successively in opposite polarity with an electrical voltage for generating two successive opposite-pole pulse signals.

6. The electrode arrangement according to claim 1 wherein the control device emits the alternating high voltage to the at least one electrode such that an electrical power is less than 10 W;

the voltage pulses are bipolar;

an electrical AC voltage is between ±1 kV and ±100 kV; and/or an alternating electrical frequency is between 100 Hz and 100 MHZ.

7. An electrode arrangement for forming a dielectric barrier discharge between at least one electrode and a surface to be treated of an electrically conductive body, said surface acting as a ground electrode, comprising:

a dielectric that completely covers the at least one electrode to the surface to be treated, wherein said dielectric forms a contact side for the surface to be treated; and a control device that comprises a high-voltage stage for supplying the at least one electrode with an alternating high voltage required for generating a plasma, wherein the control device emits the alternating high voltage to the at least one electrode in individual pulse signals, and wherein the control device is configured to generate two successive opposite-pole pulse signals in damped oscillations such that an initial half-wave of a first pulse signal has an opposite polarity to an initial half-wave of a subsequent second pulse signal, and feed the opposite-pole pulse signals successively to the same at least one electrode, wherein the control device emits the individual pulse signals to the at least one electrode such that a number of pulse signals with a first polarity are emitted one after the other and then a same number of pulse signals with a second polarity opposite to the first polarity are emitted one after the other, and wherein the number of pulse signals of the first polarity is smaller than or equal to ten.

* * * * *